United States Patent [19]
Wendt

[11] Patent Number: 5,109,711
[45] Date of Patent: May 5, 1992

[54] PROBE FOR SAMPLING PARTICULATES IN GASES FROM FLUES

[75] Inventor: Horst Wendt, Erlangen, Fed. Rep. of Germany

[73] Assignee: Fag Kugelfischer Georg Schafer, Fed. Rep. of Germany

[21] Appl. No.: 503,523

[22] Filed: Apr. 2, 1990

[30] Foreign Application Priority Data

Apr. 1, 1989 [EP] European Pat. Off. .......... 89105779

[51] Int. Cl.⁵ .............................................. G01N 1/22
[52] U.S. Cl. .................... 73/863.11; 73/863.03
[58] Field of Search .......... 73/863.11, 863.12, 864.73, 73/864.74, 864.33, 863.81, 863.83, 863.84, 863.02, 863.03

[56] References Cited

U.S. PATENT DOCUMENTS

| | | | |
|---|---|---|---|
| 3,106,843 | 10/1963 | Luxl | 73/863.12 |
| 3,793,887 | 2/1974 | Anderson et al. | 73/863.11 X |
| 3,800,595 | 4/1974 | Vincent | 73/863.21 X |
| 3,917,454 | 11/1975 | Clark | 73/863.11 |
| 3,960,500 | 6/1976 | Ross et al. | 73/863.11 X |
| 4,004,882 | 1/1977 | Byrne et al. | 73/863.12 X |
| 4,061,467 | 12/1977 | Becker et al. | 73/863.11 X |
| 4,336,721 | 6/1982 | Curtis | 73/863.11 |
| 4,344,917 | 8/1982 | Schorno | 73/863.11 X |
| 4,414,857 | 11/1983 | Brazhnikov et al. | 73/863.11 |
| 4,856,352 | 8/1989 | Daum et al. | 73/863.12 |
| 4,974,455 | 12/1990 | McGowan et al. | 73/863.12 |
| 5,033,318 | 7/1991 | Wendt | 73/863.03 |

FOREIGN PATENT DOCUMENTS

| | | | |
|---|---|---|---|
| 424040 | 4/1974 | U.S.S.R. | 73/863.11 |
| 463029 | 3/1975 | U.S.S.R. | 73/863.11 |
| 802247 | 10/1958 | United Kingdom | 73/863.12 |

OTHER PUBLICATIONS

"Beckman Modular Sample Conditioners"; Bulletin SC-4034; 20 page brochure by Beckman Instruments, Inc. of Fullerton, Calif.; published by Apr. 1963 (probably 8–1962).

Primary Examiner—Tom Noland
Attorney, Agent, or Firm—Ostrolenk, Faber, Gerb & Soffen

[57] ABSTRACT

The probe is directed toward removal and sampling particulates in possibly corrosive gases in flues. A flue gas removal tube removes flue gas from a suction nozzle and feeds it into a mixed gas feed tube, the inlet of which is of a wider diameter than the outlet portion of the flue gas removal tube. A fresh air tube surrounds the mixed gas feed tube, and fresh air flows down the fresh air tube flows down the fresh air tube and then up the mixed gas feed tube along with removed flue gas. Heating coils in the fresh air tube heat both the fresh air and the mixed gas to a temperature above the prevailing dew point. A closure spaced from the outlet from the fresh air tube and the inlet to the mixed gas feed tube has a funnel shaped development which reduces eddying of fresh air and of outgoing gases. Pitot tubes determine the pressure difference in the flue as well as in the fresh air and mixed gas removal tubes and adjust the respective flows.

16 Claims, 1 Drawing Sheet

PROBE FOR SAMPLING PARTICULATES IN GASES FROM FLUES

BACKGROUND OF THE INVENTION

The present invention relates to a probe for removing and sampling particulates in possibly corrosive gases in flues or chimneys. The probe is, in turn, connected with apparatus for measuring the state of the flue gas. See for example, European patent application 89 105 780.4, filed Apr. 1, 1989 and its corresponding U.S. application Ser. No. 503260, filed Apr. 2, 1990 now U.S. Pat. No. 5,033,318.

Such probes are known. They typically comprise four tubes of equal size arranged in a circle and spaced apart by spacing disks. They are surrounded jointly by a protective tube. The four tubes include pitot tubes which determine the difference pressure in the flue and therefore are used to measure the velocity of the flue gas and include a fresh air feed tube and a mixed gas removal tube. See the above noted application on how these tubes operate and cooperate.

The known probes have various disadvantages. They require a correspondingly large space for installation. Corrosive precipitates are produced in the probe due to the constantly varying dew point of the gases removed.

SUMMARY OF THE INVENTION

The object of the present invention is to provide a probe which is of compact construction and which also prevents the occurrence of corrosive condensation within the probe.

The sampling probe of the invention removes possibly corrosive gases from flues. It includes a flue gas removal tube which receives flue gases from a suction nozzle. There is a mixed gas feed tube into which the flue gas removal tube empties. The mixed gas feed tube has a larger entrance than the exit from the flue gas removal tube. This permits entry of other gases into the mixed gas removal tube. There is a fresh air tube which is around and is larger than the mixed gas feed tube. Fresh air is fed down the fresh air tube to the enlarged entrance of the mixed gas feed tube, so that fresh air is mixed with the removed flue gas in the entrance to the mixed gas tube.

According to a first feature of the invention, heating means are disposed in the fresh air tube to heat both the fresh air moving down the fresh air tube and the mixed gas moving up the mixed gas tube, both preferably to a temperature above the prevailing dew point of both of the gases.

There is a housing closure below the exit from the fresh air tube and just below the entrance to the mixed air tube. The closure has a conical or funnel shaped development. It has been found advantageous to provide, at the place within the probe where the fresh air is mixed with the removed off-gases, a funnel shaped development, the funnel shape of which is developed as a function of the nature and quantity of the corrosive gas to be expected so that no precipitation of dust components results due to an eddying of fresh air and offgases.

BRIEF DESCRIPTION OF THE DRAWING

Other objects and features of the invention will become apparent from an illustrative embodiment of the invention shown in the drawings.

DESCRIPTION OF THE PREFERRED EMBODIMENT

Figure 1:
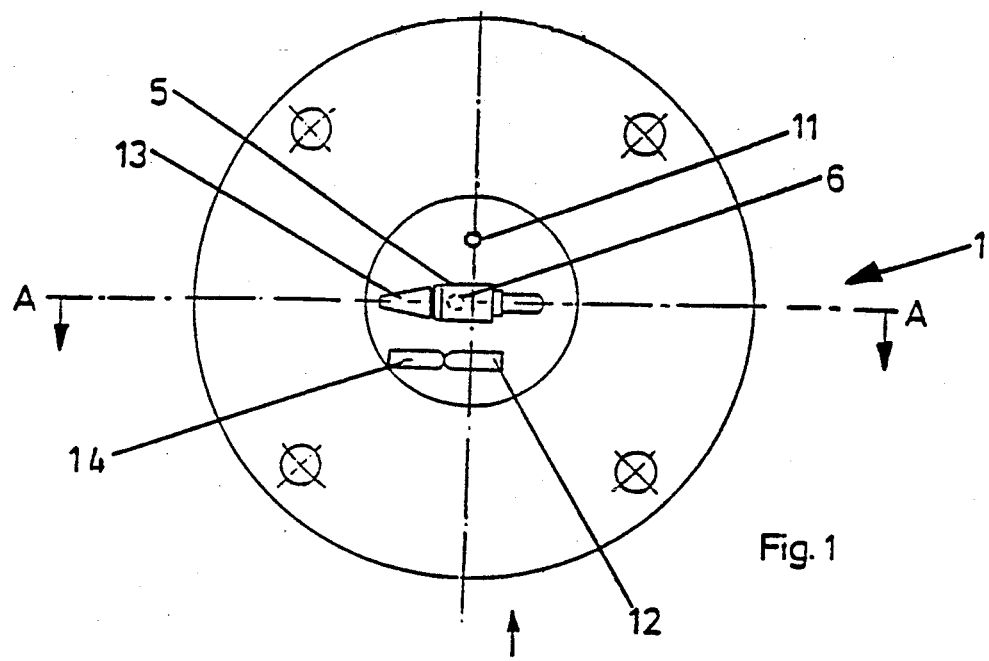
FIG. 1 is a top view of the probe.
Figure 2:
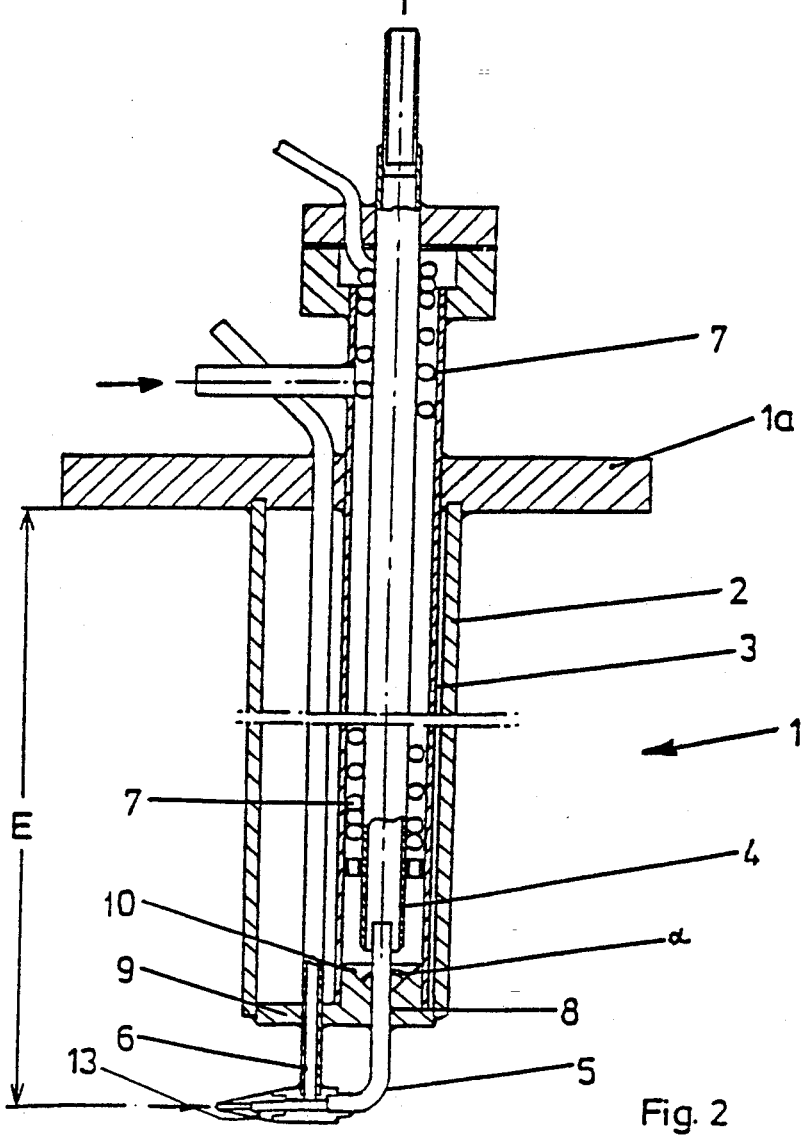
FIG. 2 is a section through the probe along the line A—A of FIG. 1.

The probe of the invention is used with a particulate content measuring apparatus like that disclosed in the above noted U.S. application Ser. No. 503,200, filed Apr. 2, 1990.

The probe 1 is fastened by the flange 1a to a flue (not shown) such that the portion E of the probe 1 extends into the flue. The tubular probe 1 has an outer protective tube 2. Within that tube 2 are disposed a fresh air tube 3 and a mixed gas feed tube 4 concentrically arranged within the fresh air tube 3. A flue gas removal tube 5 extends up into the lower end of the mixed gas feed tube 4. The head of the flue gas removal tube 5 terminates in a suction nozzle 13. Just after the inlet to the nozzle 13, there branches off a zero pressure tube 6, which is connected to a difference pressure controller, not shown in the drawing. Within the fresh air tube 3 there is a controllable heating means 7, for instance, an electric heating coil, which heats both the fresh air flowing through the fresh air tube 3 and the gaseous mixture which flows through the mixed gas feed tube 4. The gases are heated to a temperature above the prevailing dew point of the gases.

The bottom end of the fresh air tube 3 is provided with a housing closure 9, which has a housing passage 8 through it for the flue gas removal tube 5 and a funnel shaped development 10 facing upwardly within the probe 1. The angle α of the funnel shaped development 10 is a function of the nature and quality of the corrosive gas to be removed and is selected so that no eddying takes place between fresh air and outgoing gases which could result in precipitation of dust.

The pitot tubes necessary for measuring the pressure difference in the flue, which comprise the total pressure tube 14, the tube 12 required for the static pressure measurement, and a tube 6 which merges into the flue gas removal tube, together with its pressure tube 11 required also for measuring the static pressure, are integrated into the probe 1.

The probe is operated in the following manner. Outgoing air is drawn via suction nozzle 13 from the flue, not shown, and up the tube 4. At the same time, fresh air flows under pressure down through the fresh air tube 3 to the funnel shaped development 10 in the housing closure 9 so that fresh air and outgoing mix with each other at the development 10 and are transported through the mixed gas feed tube 4 to a measurement point (dust filter) not shown.

The different velocities of flow in the flue are conducted by the pressure differences in the tubes 14, 12, 6 and 11 to a difference pressure controller, not shown, which then so regulates the feed of fresh air corresponding to the velocity of flow of the outgoing gases in the flue that an identical velocity or isokinetic removal of the partial stream of gas always takes place. Note again the above noted U.S. application which details the apparatus in which this probe is included.

In order that no condensate forms within the probe 1, both the fresh air tube 2 and the mixed gas feed tube 4 are heated jointly via a controllable heating means 7 in each case to above the temperature of the prevailing dew point.

What is claimed is:

1. A probe for the removal of flue gases from a flue, comprising
 a flue gas removal tube, an inlet suction nozzle on the flue gas removal tube, an outlet from the flue gas removal tube;
 a mixed gas feed tube having an inlet, the outlet from the flue gas removal tube extending into the inlet of the mixed gas feed tube, the inlet of the mixed gas feed tube being larger than the outlet of the flue gas removal tube which outlet is in the inlet of the mixed gas feed tube, leaving a remaining entrance area into the mixed gas feed tube;
 a fresh air tube extending along the mixed gas feed tube, the fresh air tube having an outlet therefrom for fresh air, and the fresh air tube outlet being located near to so as to communicate with the inlet to the mixed gas feed tube, such that fresh air from the fresh air tube outlet enters the mixed gas feed tube inlet along with flue gas from the flue gas removal tube;
 heating means arranged in the fresh air tube, and the fresh air tube being along the mixed gas feed tube so that the heating means heats both the fresh air in the fresh air tube and the mixed gas in the mixed gas feed tube, the heating means being adapted to heat the gas in both tubes to a temperature above the respective prevailing dew points of those gases.

2. A probe for the removal of flue gases from a flue, comprising
 a flue gas removal tube, an inlet suction nozzle on the flue gas removal tube, an outlet from the flue gas removal tube;
 a mixed gas feed tube having an inlet, the outlet from the flue gas removal tube extending into the inlet of the mixed gas feed tube, the inlet of the mixed gas feed tube being larger than the outlet of the flue gas removal tube which outlet is in the inlet of the mixed gas feed tube, leaving a remaining entrance area into the mixed gas feed tube;
 a fresh air tube extending along the mixed gas feed tube, the fresh air tube having an outlet therefrom for fresh air, and the fresh air tube outlet being located near to so as to communicate with the inlet to the mixed gas feed tube, such that fresh air from the fresh air tube outlet enters the mixed gas feed tube inlet along with flue gas from the flue gas removal tube;
 heating means arranged in the fresh air tube, and the fresh air tube being along the mixed gas feed tube so that the heating means heats both the fresh air in the fresh air tube and the mixed gas in the mixed gas feed tube, the heating means being adapted to heat the gas in both tubes to a temperature above the respective prevailing dew points of those gases; and further wherein
 the fresh air tube is around the mixed gas feed tube, the fresh air tube has a larger diameter than the mixed gas feed tube and the fresh air tube has an outlet end near the inlet end of the mixed gas feed tube.

3. The probe of claim 2, wherein the flue gas removal tube portion in the inlet of the mixed gas feed tube has a smaller diameter than the mixed gas feed tube there, leaving a space for entrance of fresh air into the mixed gas feed tube around the outside of the flue gas removal tube, the heating means being located in the fresh air tube around the mixed air tube.

4. The probe of claim 3, wherein the outlet of the fresh air tube is directed in one direction and the air inlet into the mixed air tube is directed in the opposite direction, the probe including a closure located shortly beyond the outlet from the fresh air tube and shortly before the inlet to the mixed gas tube, and the flue gas removal tube extending through the closure into the mixed gas feed tube.

5. The probe of claim 4, wherein the closure has a funnel shaped development which opens and widens toward the outlet from the fresh air tube and towards the inlet to the mixed gas feed tube.

6. The probe of claim 3, further comprising a protective tube around the flue gas removal tube, the mixed gas feed tube and the fresh air tube, for protecting these elements from exposure to the flue.

7. The probe of claim 6, further comprising sensing tubes in the protective tube which sense pressure differences for use in controlling flow in the fresh air tube.

8. The probe of claim 2, wherein the heating means comprise electric coils.

9. A probe for the removal of flue gases from a flue, comprising
 a flue gas removal tube, an inlet suction nozzle on the flue gas removal tube, an outlet from the flow gas removal tube;
 a mixed gas feed tube having an inlet, the outlet from the flue gas removal tube extending into the inlet of the mixed gas feed tube, the inlet of the mixed gas feed tube being larger than the outlet of the flue gas removal tube which outlet is in the inlet of the mixed gas feed tube, leaving a remaining entrance area into the mixed gas feed tube;
 a fresh air tube extending along the mixed gas feed tube, the fresh air tube having an outlet therefrom for fresh air, and the fresh air tube outlet being located near to so as to communicate with the inlet to the mixed gas feed tube, such that fresh air from the fresh air tube outlet enters the mixed gas feed tube inlet along with flue gas from the flue gas removal tube;
 heating means arranged in the fresh air tube, and the fresh air tube being along the mixed gas feed tube so that the heating means heats both the fresh air in the fresh air tube and the mixed gas in the mixed gas feed tube, the heating means being adapted to heat the gas in both tubes to a temperature above the respective prevailing dew points of those gases; and further comprising
 sensing tubes which sense pressure differences for use in controlling flow in the fresh air tube.

10. The probe of claim 9, wherein:
 the fresh air tube is around the mixed gas feed tube and the fresh air tube has a larger diameter than the mixed gas feed tube and the fresh air tube has an outlet end near the inlet end of the mixed gas feed tube.

11. The probe of claim 10, wherein the flue gas removal tube portion in the inlet of the mixed gas feed tube has a small diameter than the mixed gas feed tube there, leaving a space for entrance of fresh air into the mixed gas feed tube around the outside of the flue gas removal tube, the heating means being located in the fresh air tube around the mixed air tube.

12. The probe of claim 11, wherein the outlet of the fresh air tube is directed in one direction and the air inlet into the mixed air tube is directed in the opposite direction, the probe including a closure located shortly beyond the outlet from the fresh air tube and shortly before the inlet to the mixed gas tube, and the flue gas removal tube extending through the closure into the mixed gas feed tube.

13. The probe of claim 12, wherein the closure has a funnel-shaped development which opens and widens toward the outlet from the fresh air tube and towards the inlet to the mixed gas feed tube.

14. The probe of claim 11, further comprising a protective tube around the flue gas removal tube, the mixed gas feed tube and the fresh air tube, for protecting these elements from exposure to the flue.

15. The probe of claim 14, further comprising sensing tubes in the protective tube which sense pressure differences for use in controlling flow in the fresh air tube.

16. The probe of claim 10, wherein the heating means comprise electric coils.

* * * * *